United States Patent [19]

Sato et al.

[11] Patent Number: 4,593,048

[45] Date of Patent: Jun. 3, 1986

[54] BASE COMPOSITION FOR EXTERNAL PREPARATIONS, PHARMACEUTICAL COMPOSITION FOR EXTERNAL USE AND METHOD OF PROMOTING PERCUTANEOUS DRUG ABSORPTION

[75] Inventors: Susumu Sato; Umiko Takakura; Mitsuru Tamada, all of Ibaraki, Japan

[73] Assignee: Nitto Electric Industrial Co., Ltd., Osaka, Japan

[21] Appl. No.: 503,195

[22] PCT Filed: Sep. 24, 1982

[86] PCT No.: PCT/JP82/00385

§ 371 Date: May 13, 1983

§ 102(e) Date: May 13, 1983

[87] PCT Pub. No.: WO83/01000

PCT Pub. Date: Mar. 31, 1983

[30] Foreign Application Priority Data

Sep. 28, 1981 [JP] Japan ................. 56-154485

[51] Int. Cl.$^4$ ............................................. A61K 47/00
[52] U.S. Cl. .................... 514/778; 514/772; 514/789
[58] Field of Search ............... 424/350; 514/772, 778, 514/789

[56] References Cited

U.S. PATENT DOCUMENTS 4,309,414 1/1982 Inagi et al. ..................... 424/81

FOREIGN PATENT DOCUMENTS 13553 2/1973 Japan .
 8919 2/1973 Japan .

OTHER PUBLICATIONS

Chem. Abst., 97 (150740h) (1982), 98 (221852e)–1983, & 89 (48905p) (1978).

Primary Examiner—Stanley J. Friedman
Attorney, Agent, or Firm—Wenderoth, Lind & Ponack

[57] ABSTRACT

A composition capable of promoting the skin permeation or percutaneous absorption of a drug, which comprises a lower alcohol and at least one member of the group consisting of a saturated aliphatic hydrocarbon containing 5 to 20 carbon atoms, which may optionally be halogen-substituted, a monohydric alcohol ester of an aliphatic carboxylic acid, which contains 13 to 24 carbon atoms, and an ether containing 8 to 16 carbon atoms with one ether bondage in the molecule; and an external preparation containing the above composition as a base.

7 Claims, No Drawings

4,593,048

BASE COMPOSITION FOR EXTERNAL PREPARATIONS, PHARMACEUTICAL COMPOSITION FOR EXTERNAL USE AND METHOD OF PROMOTING PERCUTANEOUS DRUG ABSORPTION

TECHNICAL FIELD

This invention relates to a base composition capable of increasing the percutaneous absorption of drugs, to a pharmaceutical composition for external use in which said base composition is used, and to a method of promoting the percutaneous absorption of drugs.

BACKGROUND ART

The drugs so far administered to the outer skin have served the purpose of producing a local effect on the outer skin or hypodermal tissues, such as a bactericidal, disinfecting or analgesic effect. However, in recent years, attempts have also been made to administer drugs having a systemic activity to the outer skin, instead of by peroral administration or injection. The percutaneous administration of a drug, particularly a systemic drug, has the following advantages, among others: the drug efficacy can easily be maintained for a long while; the rate of drug absorption can easily be controlled, so that adverse effects due to overdosage can be minimized; since the drug is sparingly metabolized in the liver by the first pass effect as found in the case of oral administration, the drug can be used effectively; and even a drug possibly causing gastrointestinal disorders upon oral administration, such as indomethacin, can be administered safely.

However, the normal skin, which has a body-protecting action, is generally capable of resisting drug absorption or permeation. Therefore, drugs (especially systemic drugs), when simply administered in the conventional forms of ointment, lotion and so on, can scarcely be absorbed into the body in amounts sufficient to produce a satisfactory pharmacological effect.

DISCLOSURE OF THE INVENTION

Under these circumstances, the present inventors conducted intensive research and, as a result, obtained the following findings:

(1) That a composition comprising a lower alcohol and at least one adjuvant selected from among a saturated aliphatic hydrocarbon containing 5 to 20 carbon atoms, which may optionally be halogen-substituted, a carboxylic acid alcohol ester containing 13 to 24 carbon atoms in total, and an ether can improve the skin permeation and percutaneous absorption of drugs, and (2) That the above-mentioned composition can be used as a base for drugs to be applied to the skin. These findings have led to the present invention.

Accordingly, a primary object of the present invention is to provide a base composition for external preparations which is capable of increasing the skin permeation and percutaneous absorption of drugs.

A second object of the invention is to provide a pharmaceutical composition for external use which is satisfactory in skin permeation and percutaneous absorption of drugs.

A third object of the invention is to provide a method of increasing the skin permeation and percutaneous absorption of drugs.

Thus, the present invention provides:

(1) A base composition for external preparations which comprises a lower alcohol and at least one adjuvant selected from among a saturated aliphatic hydrocarbon containing 5 to 20 carbon atoms, which may optionally be halogen-substituted, a carboxylic acid alcohol ester containing 13 to 24 carbon atoms in total, and an ether;

(2) A pharmaceutical composition for external use which comprises a drug and the above-mentioned base composition; and (3) A method of promoting the skin permeation and percutaneous absorption of a drug which comprises administering the drug to the skin together with the above-mentioned base composition.

The lower alcohol to be used in the practice of the present invention is preferably a monohydric lower alcohol containing 1 to 4 carbon atoms, including methyl alcohol, ethyl alcohol, n-propyl alcohol, isopropyl alcohol, n-butyl alcohol, isobutyl alcohol, sec-butyl alcohol and t-butyl alcohol. Among these, ethyl alcohol is particularly preferred.

The saturated aliphatic hydrocarbon containing 5 to 20 carbon atoms, which may optionally be halogen-substituted, may be acylic (straight-chained or branched) or cyclic. The straight-chained one includes among others n-pentane, n-hexane, n-heptane, n-octane, n-nonane, n-decane, n-undecane, n-dodecane, n-tetradecane, n-hexadecane, n-octadecane and n-eicosane, among which those containing 6 to 16 carbon atoms are preferred. The branched one includes among others 2-methylpentane, 2,3-dimethylhexane, 2,2,4,4,6,8,8-heptamethylnonane and limonene, and preferably contains 6 to 16 carbon atoms. The cyclic one includes monocyclic or bicyclic ones which contain 6 to 12 carbon atoms, such as cyclohexane, cyclododecane and decalin. The halogen as the substituent is, for example, chlorine or bromine. As the halogen-substituted adjuvant, there may be mentioned saturated, straight-chained, halogenated hydrocarbons containing 8 to 16 carbon atoms, such as octyl bromide, dodecyl bromide, hexadecyl bromide and dodecyl chloride. The number of the halogen substituents is 1 or 2, preferably 1.

The carboxylic acid moiety of the carboxylic acid alcohol ester containing 13 to 24 carbon atoms in total is preferably from an aliphatic carboxylic acid which contains 12 to 18 carbon atoms and more preferably is a fatty acid. The alcohol moiety is preferably a monohydric alcohol containing 1 1 to 6, more preferably 3 to 6 carbon atoms, such as methyl alcohol, ethyl alcohol, n-propyl alcohol, iso-propyl alcohol, n-butyl alcohol, iso-butyl alcohol, n-pentyl alcohol or n-hexyl alcohol. Preferred examples of said carboxylic acid alcohol ester are hexyl laurate, isopropyl myristate, isopropyl palmitate and butyl stearate.

The ether includes ethers containing 8 to 16 carbon atoms with one ether bondage per molecule, such as dibutyl ether, dihexyl ether, dioctyl ether, methoxydodecane, ethoxydodecane and 1,8-cineole.

The base composition in accordance with the present invention is prepared by adding the adjuvant to the lower alcohol. The adjuvant is incorporated in an amount of 1 to 50 percent by weight, preferably 5 to 30 percent by weight, based on the lower alcohol. Said base composition may of course contain any other pharmaceutically acceptable additives.

The pharmaceutical composition for external use in accordance with the present invention is prepared by incorporating a drug into the base composition. The drug to be incorporated is not particularly limited so long as it is applicable to the skin. However, the drug should preferably have a solubility in the lower alcohol of 0.5 to 10%, more preferably 1 to 5%.

The drug species having a solubility in the above range, when incorporated into the base composition according to the present invention, can be distributed to the skin to an increased extent, hence percutaneously absorbed to an improved extent. The "solubility" as used herein means the solubility as measured by adding the drug in excess to the lower alcohol warmed at 20° C. for dissolution, stirring the mixture occasionally and, after 24 hours, separating the supernatant and assaying the same for the drug by absorptiometry.

The drug is incorporated in an amount sufficient to produce the desired pharamacological effect. Such amount may vary depending on the drug species, body weight and condition of the patient, and so on. Therefore, the drug amount may be adequately selected depending on these conditions. Generally, from the percutaneous absorption viewpoint, the drug is preferably used in an amount of 0.01 to 20 percent by weight, more preferably 0.1 to 10 percent by weight, based on the total amount of the lower alcohol and adjuvant.

Since the dose of a drug can be adjusted by increasing or decreasing the skin surface area to which the pharmaceutical composition is applied, the amount of the drug incorporated in the composition is not always limited to the above range.

For those drugs that are used for producing a local effect against diseases of the outer skin or hypodermal tissues, for instance, the conventional external preparations are also effective to a certain extent. Therefore, the pharmaceutical composition in accordance with the present invention becomes more significant when it contains a drug which is expected to produce a systemic effect.

To be concrete, the drug includes, among others, benzodiazepines (e.g. diazepam, nitrazepam, flunitrazepam, lorazepam, prazepam, fludiazepam, clonazepam), diuretics [e.g. thiazides (e.g. bendrofluomethazide, polythiazide, methylclothiazide, trichlormethiazide, cyclopenthiazide, benzylhydrochlorothiazide, hydrochlothiazide, bumetanide)], hypotensives, (e.g. clonidine), antihistaminics [e.g. aminoethers (e.g. diphenhydramine, carbinoxamine, diphenylpyraline), ethylenediamines (e.g. phenbenzamine), monoamines (e.g. chlorpheniramine)], nonsteroid antiinflammatories (e.g. indomethacin, ibuprofen, ibufenac, alclofenac, diclofenac, mefanamic acid, flurbiprofen, flufenamic acid, ketoprofen), anti-malignant-tumor agents (e.g. 5-fluorouracil, 1-(2-tetrahydrofuryl)-5-fluorouracil, cytarabine, broxuridine), steroidal antiinflammatories (e.g. cortisone, hydrocortisone, prednisolone, prednisone, triamcilonone, dexamethosone, betamethasone), antiepileptics (e.g. ethosuximide), antiarrythmic agents (e.g. ajmalin, projmalin, pindolol, propranolol, quinidine), psychotropic agents (e.g. clofluperidol, trifluperidol, haloperidol, moperone), scopolamines (e.g. methylscopolamine, butylscopolamine), chlorpromazine, atropines (e.g. methylatropine bromide, methylanisotropine bromide), vasodilators (e.g. isosorbide dinitrate, nitroglycerin, pentaerythritol tetranitrate, propatyl nitrate, dipyridamole), antibiotics [e.g. tetracyclines (e.g. tetracycline, oxytetracycline, metacycline, doxycycline, minocycline)], chloramphenicol and erythromycins.

The pharmaceutical composition for external use in accordance with the present invention is administered to the skin either as it is or in the form of an external preparation, such as ointment, plaster, lotion, adhesive tape preparation, impregnation or gel, made by addition of a known third component and so on. The impregnation is prepared, for example, by allowing an appropriate adsorbent (e.g. gauze, filter paper, porous membrane) to be impregnated with said pharmaceutical composition for external use as it is or with a composition prepared by further incorporating a known third component into said pharmaceutical composition, and is generally applied to the skin under fixation to the skin by means of an adhesive tape. The gel is prepared, for instance, for producing a gel using a gelling agent for alcohols [e.g. GELOL D (Shin Nippon Rika Kogyo)] and spreading the gel onto a support member. The base for the adhesive tape preparation may be a per se known one, such as an acrylic copolymer, a polyvinyl ether compound or an adhesive rubber mixture. Other external preparations also can be prepared easily by the per se known techniques.

The following examples and test examples illustrate the present invention in more detail. However, they are by no means limitative of the present invention.

EXAMPLES 1–27

Basic formulation
(1) Diazepam: 3 g
(2) Lower alcohol: 72 g
(3) Adjuvant: 25 g

Liquid compositions were prepared by first mixing component (3) with component (2) and further dissolving component (1) in accordance with the above basic formulation using the lower alcohols and adjuvants specifically indicated in Table 1.

COMPARATIVE EXAMPLES 1–3

(1) Diazepam: 3 g
(2) Lower alcohol: 97 g

Liquid compositions were prepared by dissolving the above component (1) in component (2) specifically indicated in Table 1.

COMPARATIVE EXAMPLE 4

(1) Diazepam: 3 g
(2) Dimethyl sulfoxide: 97 g

TEST EXAMPLE 1

Each liquid composition of Examples 1–27 and Comparative Examples 1–3 was tested for skin permeation of the drug using a diffusion cell, 2 cm inside diameter, fitted with an excised rat abdominal skin piece, and 0.5 ml of the composition. The results are shown in Table 1.

(Method of measurement)

The glass diffusion cell was fitted with the rat skin piece in the manner such that the outer side of the skin was brought into contact with the above liquid composition and the inner side of the skin with physiological saline, and the drug portion that had permeated the skin into the physiological saline was extracted with benzene and assayed by spectrophotometry.

TABLE 1

| Example No. | Lower alcohol | Adjuvant | Drug permeation 0-8 hr, μg/cm² mean ± S.E. |
|---|---|---|---|
| 1 | Ethyl alcohol | n-Hexane | 260 ± 45 |
| 2 | " | Dodecane | 250 ± 38 |
| 3 | " | Hexadecane | 145 ± 31 |
| 4 | " | Isooctane | 187 ± 35 |
| 5 | " | Cyclohexane | 188 ± 20 |
| 6 | " | Cyclododecane | 67 ± 15 |
| 7 | " | Limonene | 133 ± 23 |
| 8 | " | Methyl laurate | 152 ± 30 |
| 9 | " | Hexyl laurate | 96.7 ± 8.9 |
| 10 | " | Isopropyl myristate | 142 ± 27 |
| 11 | " | Butyl stearate | 134 ± 25 |
| 12 | " | Octyl bromide | 120 ± 18 |
| 13 | " | Dodecyl bromide | 180 ± 29 |
| 14 | " | Hexadecyl bromide | 95 ± 96 |
| 15 | " | Dodecyl chloride | 181 ± 92 |
| 16 | " | Hexyl ether | 137 ± 16 |
| 17 | " | 1,8-Cineole | 150 ± 21 |
| 18 | " | n-Eicosane | 78 ± 17 |
| 19 | " | n-Pentane | 190 ± 13 |
| Comparative 1 | Ethyl alcohol | — | 36 ± 9 |
| Example 20 | Isopropyl alcohol | n-Dodecane | 232 ± 29 |
| Example 21 | Isopropyl alcohol | Pristane | 166 ± 22 |
| Comparative 2 | Isopropyl alcohol | — | 32 ± 4 |
| Example 22 | tert-Butyl alcohol | n-Hexane | 178 ± 14 |
| 23 | tert-Butyl alcohol | n-Dodecane | 312 ± 17 |
| 24 | tert-Butyl alcohol | n-Hexadecane | 216 ± 22 |
| 25 | tert-Butyl alcohol | Pristane | 237 ± 31 |
| 26 | tert-Butyl alcohol | Isostearyl palmitate | 158 ± 11 |
| 27 | tert-Butyl alcohol | Butyl stearate | 185 ± 15 |
| Comparative 3 | tert-Butyl alcohol | — | 37 ± 7 |

TEST EXAMPLE 2

A 4 cm² piece of gauze impregnated with one of the compositions of Examples 2 and 10 and Comparative Examples 1 and 4 was fixed on the clipped back of an albino rabbit weighing 3.5 kg. Blood samples were taken at time intervals, extracted and concentrated in the conventional manner, and assayed for the drug by gas chromatography using an electron capture detector. The results obtained are shown in Table 2.

TABLE 2

| | Blood concentration, ng/ml After | | | | |
|---|---|---|---|---|---|
| | 1 hr | 2 hrs | 4 hrs | 6 hrs | 8 hrs |
| Example 2 | 33 | 98 | 107 | 83 | 45 |
| Example 10 | 40 | 130 | 162 | 103 | 61 |
| Comparative Example 1 | 15 | 14 | 24 | 30 | 23 |
| Comparative Example 4 | 121 | 140 | 140 | 63 | 50 |

EXAMPLE 28 AND TEST EXAMPLE 3

(1) Clonidine base: 0.8 g
(2) Ethyl alcohol: 75.2 g
(3) Isopropyl myristate: 25 g Components (2) and (3) were mixed, and component (1) was dissolved in the mixture. A 0.5 cm² piece of gauze was impregnated with the resulting solution and applied to the clipped abdominal area of a Wistar strain rat, and the caudal artery pressure was measured. The results are shown in Table 3. The caudal artery pressure data obtained with the liquid compositions of Comparative Examples 5 and 6 as the controls are also shown in Table 3.

COMPARATIVE EXAMPLE 5

(1) Clonidine base: 0.8 g
(2) Ethyl alcohol: 97.2 g

COMPARATIVE EXAMPLE 6

(1) Clonidine base: 0.8 g
(2) Dimethyl sulfoxide: 99.2 g

TABLE 3

| | Caudal artery pressure, mmHg After | | | | |
|---|---|---|---|---|---|
| | 0 hr | 1 hr | 3 hrs | 5 hrs | 7 hrs |
| Example 28 | 120 | 96 | 70 | 65 | 78 |
| Comparative Example 5 | 119 | 100 | 97 | 86 | 92 |
| Comparative Example 6 | 128 | 107 | 95 | 87 | 99 |
| No treatment | 125 | 113 | 122 | 119 | 127 |

EXAMPLE 29

(1) Indomethacin: 1.0 g
(2) Ethyl alcohol: 76.0 g
(3) n-Dodecane: 23.0 g

The above components were mixed for dissolution in one and the same vessel to give a liquid composition.

COMPARATIVE EXAMPLE 7

(1) Indomethacin: 1 g
(2) Ethyl alcohol: 99 g

The above component (1) was dissolved in (2).

COMPARATIVE EXAMPLE 8

(1) HIVISWAKO 104® (Wako Pure Chemical Indursties): 1.0 g
(2) Indomethacin: 1.0 g
(3) Propylene glycol: 12.0 g
(4) Ethyl alcohol: 30 g
(5) Diisopropyl adipate: 2.0 g
(6) Diisopropanolamine: 1.1 g
(7) Purified water: A sufficient amount to make 100 g (A) The component (1) was allowed to swell in 20 g of water. (B) The component (2) was dissolved in (3), (4) and (5). (C) The solution (B) was added to (A) and the mixture was stirred until complete hydration. (D) The component (6) was dissolved in 10 g of water and the solution was added to (C). After addition of the remaining amount of water, the whole mixture was stirred until it became homogeneous.

TEST EXAMPLE 4

Rat skin permeation of indomethacin

The absominal area of a Wistar strain male rat weighing 200 g was clipped with a manual hair clipper and an electric hair clipper (Braun) and then the abdominal skin was peeled off and mounted on a glass-made drug permeation cell. One of the liquid compositions of Example 29 and Comparative Examples 7 and 8 was applied to the skin in a dose of 150 mg per cm² and the skin permeation of indomethacin was determined. The results are shown in Table 4.

TABLE 4

| | Permeation of indomethacin, μg/cm² | | | |
|---|---|---|---|---|
| | 2 hrs | 4 hrs | 6 hrs | 8 hrs |
| Example 29 | 29.9 | 73.8 | 110.0 | 185.3 |
| Comparative Example 7 | 4.9 | 15.2 | 23.6 | 31.7 |
| Comparative Example 8 | 0.9 | 4.2 | 13.4 | 24.0 |

EXAMPLES 30–43

[Basic formulation]
(1) n-Decane: 25 g
(2) Ethyl alcohol: 72 g
(3) Drug: 3 g

A base was prepared by mixing component (2) with component (1), and component (3), namely the drug specifically indicated in Table 5, is added thereto to give a liquid composition.

COMPARATIVE EXAMPLES 9–22

Liquid compositions were produced in which the n-decane in Examples 30–43 was replaced by 97 g of ethyl alcohol.

TEST EXAMPLE 5

The skin permeation of the drug in each of the liquid compositions of Examples 30–43 and Comparative Examples 9–22 was measured using an excised rat abdominal skin piece mounted on a diffusion cell, 0.95 cm inside diameter, and 0.1 ml of each composition. The results are shown in Table 5.

(Method of measurement)

The glass-made diffusion cell was fitted with the rat skin piece in the manner such that the outer side of the skin was brought into contact with the above liquid composition and the inner side with physiological saline, and the drug portion which had permeated the skin into the physiological saline was extracted with chloroform. The extract was evaporated to dryness, and the residue was dissolved in methanol and assayed for the drug by spectrophotometery.

TABLE 5

| Example No. or Comparative Example No. | Drug | Drug permeation 0-24 hr, μg/cm² mean (n = 3) |
|---|---|---|
| Example 30 | Tetracycline | 24.07 |
| Compar. 9 | " | 0 |
| Example 31 | Methylscopolamine | 1649 |
| Compar. 10 | " | 927.4 |

TABLE 5-continued

| Example No. or Comparative Example No. | Drug | Drug permeation 0-24 hr, μg/cm² mean (n = 3) |
|---|---|---|
| Example 32 | Chloramphenicol | 31.17 |
| Compar. 11 | " | 21.13 |
| Example 33 | Haloperidol | 88.45 |
| Compar. 12 | " | 55.77 |
| Example 34 | Diclofenac sodium | 248.9 |
| Compar. 13 | " | 49.6 |
| Example 35 | Flurbiprofen | 254.1 |
| Compar. 14 | " | 204.6 |
| Example 36 | 1-(2-Tetrahydrofuryl)-5-fluorouracil | 484.2 |
| Compar. 15 | 1-(2-Tetrahydrofuryl)-5-fluorouracil | 103.5 |
| Example 37 | Prednisolone | 38.3 |
| Compar. 16 | " | 0 |
| Example 38 | Ethosuximide | 6253 |
| Compar. 17 | " | 3493 |
| Example 39 | Hydrochlorothiazide | 44.5 |
| Compar. 18 | " | 0 |
| Example 40 | Diphenhydramine hydrochloride | 1481.5 |
| Compar. 19 | Diphenhydramine hydrochloride | 365.1 |
| Example 41 | Mefenamic acid | 101.4 |
| Compar. 20 | " | 44.9 |
| Example 42 | Fluphenamic acid | 247.0 |
| Compar. 21 | " | 130.2 |
| Example 43 | Indomethacin | 121.7 |
| Compar. 22 | " | 21.3 |

We claim:

1. A composition which comprises a lower alcohol containing 1 to 4 carbon atoms and at least one adjuvant selected from the group consisting of (1) a saturated, acyclic, aliphatic hydrocarbon containing 6 to 16 carbon atoms, (2) a saturated cyclic, aliphatic hydrocarbon containing 6 to 12 carbon atoms, (3) a saturated, acyclic, halogenated, aliphatic hydrocarbon containing 6 to 16 carbon atoms, (4) a saturated, cyclic, halogenated, aliphatic hydrocarbon containing 6 to 12 carbon atoms, (5) an aliphatic carboxylic acid monohydric alcohol ester containing 19 to 24 carbon atoms in total wherein the carboxylic acid moiety is a fatty acid moiety containing 18 carbon atoms and the alcohol moiety contains 1 to 6 carbon atoms, and (6an acyclic ether containing 8 to 16 carbon atoms with one ether bonding per molecule, the amount of the adjuvant being 1 to 50 percent by weight based on the lower alcohol.

2. A composition according to claim 1, wherein said adjuvant comprises said (1).

3. A composition according to claim 1, wherein said adjuvant comprises said (2).

4. A composition according to claim 1, wherein said adjuvant comprises said (3).

5. A composition according to claim 1, wherein said adjuvant comprises said (4).

6. A composition according to claim 1, wherein said adjuvant comprises said (5).

7. A composition according to claim 1, wherein said adjuvant comprises said (6).

* * * * *